United States Patent [19]

Neri

[11] Patent Number: 5,013,905

[45] Date of Patent: May 7, 1991

[54] METHOD OF ELECTRO-OPTICALLY INSPECTING CIGARETTES

[75] Inventor: Armando Neri, Bologna, Italy

[73] Assignee: G.D Societa' per Azioni, Bologna, Italy

[21] Appl. No.: 357,429

[22] Filed: May 25, 1989

[30] Foreign Application Priority Data

May 31, 1988 [IT] Italy .................. 3483 A/88

[51] Int. Cl.$^5$ .................................... G01N 9/04
[52] U.S. Cl. ........................... 250/223 R; 209/536
[58] Field of Search ............ 209/535, 536, 576, 577; 250/223 R, 208.1, 572; 356/237; 358/106

[56] References Cited

U.S. PATENT DOCUMENTS 3,980,567  9/1976  Benini .................. 250/223 R
4,639,592  1/1987  Heitmann .................. 250/572

Primary Examiner—David C. Nelms
Attorney, Agent, or Firm—Marshall, O'Toole, Gerstein, Murray & Bicknell

[57] ABSTRACT

A method of electro-optically inspecting cigarettes, whereby the cigarettes are fed along a route defined by two counter-rotating conveyors, each having substantially cylindrical peripheral seats designed to cooperate with opposite halves of the lateral outer surface of the cigarettes. The exposed surface portion of each cigarette is inspected by an electro-optical device, such as a telecamera, as it travels over each conveyor, and the end of the cigarette inspected by at least a further electro-optical device; the resulting images produced by the aforementioned electro-optical devices being compared with a specimen image, and the result of said comparison being employed for determining acceptance or rejection of each cigarette.

7 Claims, 2 Drawing Sheets

METHOD OF ELECTRO-OPTICALLY INSPECTING CIGARETTES

BACKGROUND OF THE INVENTION

The present invention relates to a method of electro-optically inspecting cigarettes.

Before being fed on to a packing machine, the cigarettes coming off a manufacturing machine are usually inspected to determine conformance with a number of functional and dimensional tolerances governing, among other things, the size of the cigarettes, compactness of the tobacco at the open end, and location of both the component parts and printed portions of the cigarette.

Such inspection is usually conducted using a number of photocell assemblies located along the route travelled by the cigarettes, and each designed to supply information relative to a particular characteristic of the cigarette, which information is employed for determining acceptance or rejection of the same.

SUMMARY OF THE INVENTION

The aim of the present invention is to provide a method enabling overall on-line inspection, in one single operation, of the aesthetic and dimensional characteristics of cigarettes travelling along a manufacturing line and, in particular, inside a filter assembly machine, thus enabling elimination of at least some of the aforementioned photocell assemblies.

With this aim in view, according to the present invention, there is provided a method of electro-optically inspecting cigarettes, characterised by the fact that it comprises stages consisting in:

successively feeding said cigarettes along a route defined by two counter-rotating conveyors, each having substantially cylindrical peripheral seats designed to cooperate with respective opposite halves of the lateral outer surface of said cigarettes;

inspecting the exposed surface portion of each said cigarette by means of an electro-optical device, preferably a telecamera, as each said cigarette travels over each said conveyor;

comparing the images produced by said electro-optical devices with a specimen image; and employing the result of said comparison for determining acceptance or rejection of each said cigarette.

BRIEF DESCRIPTION OF THE DRAWINGS

A non-limiting embodiment of the invention will be described by way of example with reference to the accompanying drawings, in which.

DETAILED DESCRIPTION OF THE INVENTION

Figure 1:
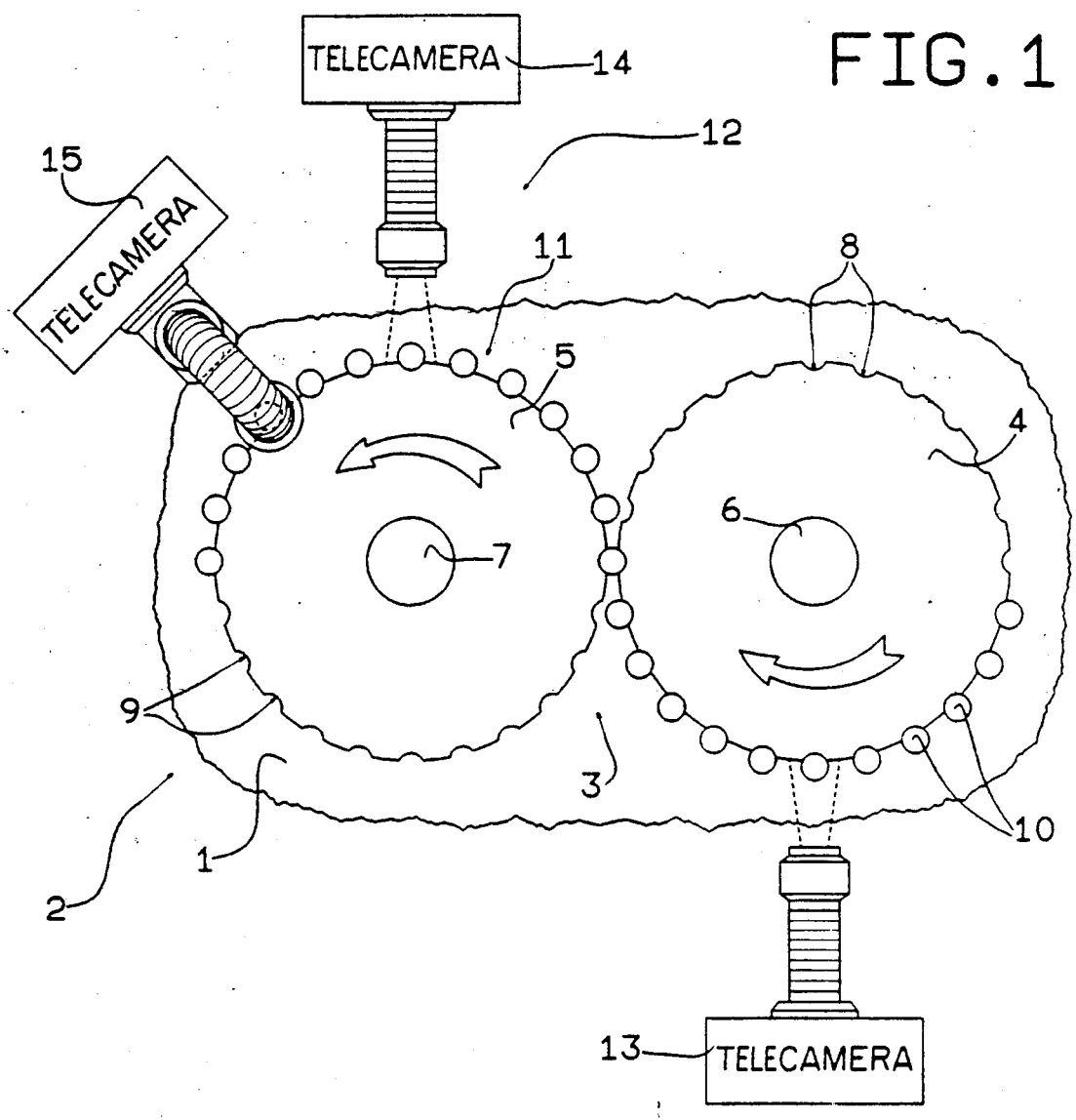
FIG. 1 shows a schematic view of part of a conveyor line on a filter assembly machine having an electro-optical inspection system embodying the method according to the present invention.

Number 1 in FIG. 1 indicates a bed portion of a filter assembly machine 2 having an internal conveyor line comprising a cigarette transfer assembly 3 supported on bed 1, and comprising two substantially tangent, counter-rotating conveyor rollers 4 and 5 fitted on to respective powered shafts 6 and 7 supported on bed 1.

Rollers 4 and 5 present respective substantially semi-cylindrical peripheral seats 8 and 9, for pneumatically retaining cigarettes 10 in known manner (not shown). Cigarettes 10 housed inside seats 8 are transferred, in known manner to seats 9 at the point of tangency between rollers 4 and 5, so as to travel, through transfer assembly 3, along a substantially S-shaped route 11 extending over an edge portion of each of rollers 4 and 5. On being transferred from roller 4 to roller 5, the covered half of each cigarette 10 formerly facing respective seat 8 is located facing outwards, and therefore exposed, inside respective seat 9.

Transfer assembly 3 features an inspection system 12 comprising a first electro-optical unit consisting of a telecamera 13 facing the portion of route 11 extending over roller 4; a second electro-optical unit consisting of a telecamera 14 facing the portion of route 11 extending over roller 5; and a third electro-optical unit consisting of a telecamera 15 located on any portion of route 11. In the example shown, telecamera 15 is located on the portion of route 11 extending over roller 5.

Inspection system 12 is controlled by a circuit 16 (FIG. 4) piloted by a counter 17. When a given cigarette 10 moves past telecamera 13, this is activated by counter 17 to produce a first image which is sent, in the form of analog signals, to an analog-digital input transducer 18 on circuit 16, which also comprises a storage device 19 for receiving the signals emitted by transducer 18.

When said cigarette 10 moves past telecamera 14, this is activated by counter 17 to produce a second image which is sent, in the form of analog signals, to a further analog-digital transducer 18 connected to the input of storage device 19.

Figure 2:
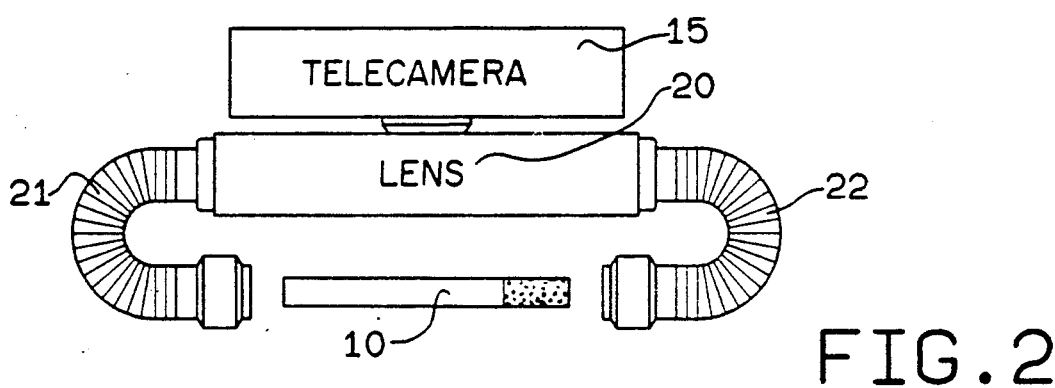
FIG. 2 shows a schematic view of a detail in FIG. 1.

When said cigarette 10 finally moves past telecamera 15, this activated by counter 17 to produce a third image which is sent, in the form of analog signals, to a third analog-digital transducer 18 also connected to the input of storage device 19. As shown in FIG. 2, the image supplied by telecamera 15 consists of two separate images, each relative to a respective end of said cigarette 10. This is made possible by virtue of lens 20 on telecamera 15 simultaneously controlling both ends of cigarette 10 via two optical fibre guides 21 and 22 having respective ends facing respective ends of cigarette 10.

According to a variation (not shown), optical guides 21 and 22 are replaced by respective mirror systems connected optically to each other and to the lens on telecamera 15 via a central prism.

Figure 3:
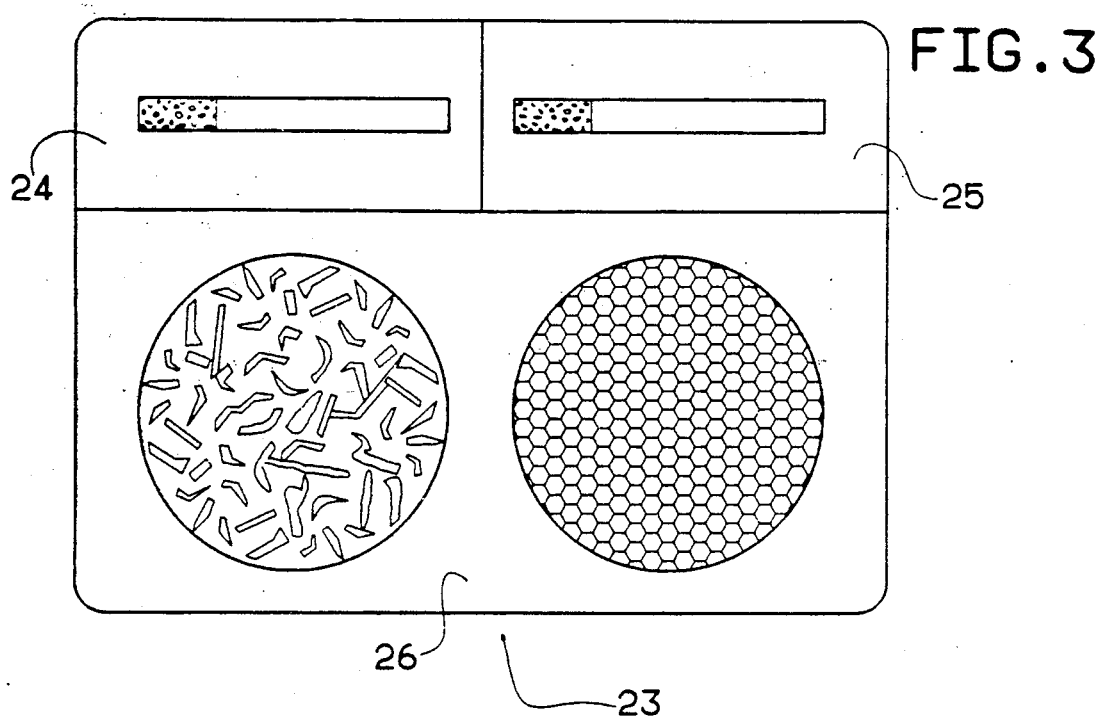
FIG. 3 shows a composite image produced by the electro-optical system in FIG. 1.

At this point, a complex image 23 (FIG. 3) of said cigarette 10 has now been formed inside storage device 19; said image comprising a first image 24 of a first side view of cigarette 10, a second image 25 of a second side view of cigarette 10, and a further image 26 showing two end views of cigarette 10.

Figure 4:
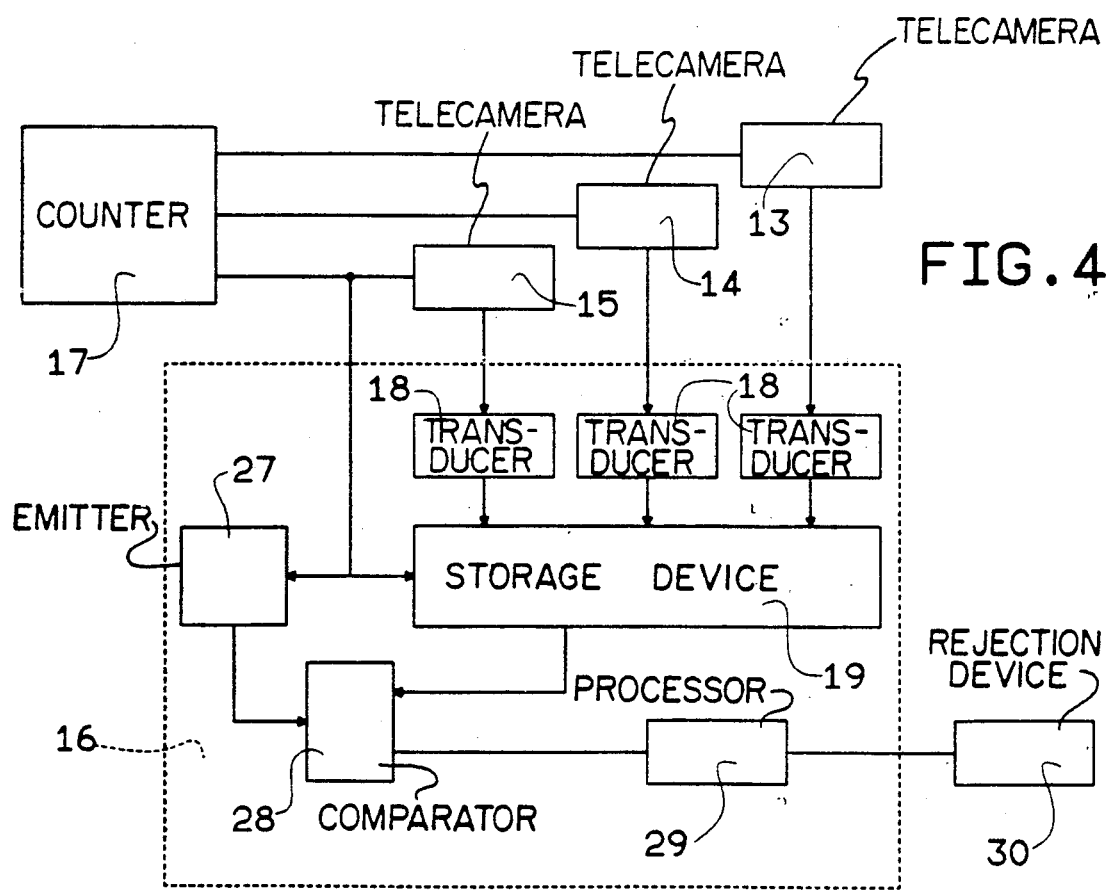
FIG. 4 shows a block diagram of a circuit controlling the electro-optical system in FIG. 1.

As shown in FIG. 4, in addition to enabling telecamera 15, counter 17 also provides simultaneously for enabling emission of complex image 23 by storage device 19, and of a specimen image by emitter 27. Image 23 and the specimen image are sent simultaneously to the inputs of a comparator 28, which detects any differences between the images, and sends the result to a processor 29 which, depending on how it is programmed, determines whether or not cigarette 10 is to be accepted or rejected, In the event of cigarette 10 being rejected, processor 29 so instructs a known type of rejection device 30 downstream from roller 5, by which cigarette 10 is subsequently rejected.

Inspection as described above, which is repeated for each cigarette 10 or according to a given sampling schedule, provides for determining whether the size of the cigarettes coming off the manufacturing machine, compactness of the tobacco at the open end, and location of both the component parts and printed portions of the cigarette, conform with specified tolerances.

I claim:

1. A method of electro-optically inspecting cigarettes comprising:

successively feeding cigarettes (10) along a route defined by two counter-rotating conveyors (4,5), each conveyor having substantially cylindrical peripheral seats (8,9) designed to cooperate with respective opposite halves of the lateral outer surface of the cigarettes (10);

inspecting the exposed surface portion of each cigarette (10) by means of an image producing electro-optical device (13,14) as each cigarette (10) travels over each conveyor (4,5);

inspecting the ends of each cigarette (10) by transmitting to another single electro-optical device (15) a first image showing one end and a second image showing an opposite end of each said cigarette (10);

comparing the images produced by the electro-optical devices (13,14,15) with a specimen image; and employing the result of said comparison for determining acceptance or rejection of each cigarette (10).

2. A method according to claim 1 in which the electro-optical device receiving the images of the cigarette ends is a single telecamera.

3. A method according to claim 1 in which the electro-optical devices (13,14) inspecting the exposed lateral surfaces of each cigarette are telecameras.

4. A method according to claim 2 in which the two end images are transmitted to said single electro-optical telecamera device (15) via optical guides (21,22).

5. Apparatus for conducting a quality control inspection of cigarettes being fed along a route comprising:

a conveyor adapted to feed a plurality of spaced apart cigarettes along a route, with the cigarettes arranged lateral to the direction of the route;

a first optical device for viewing a first end of a cigarette traveling along the route and delivering the view of the cigarette first end to an electro-optical device as a first image;

a second optical device for viewing a second end of the same cigarette traveling along the route and delivering the view of the cigarette second end to the electro-optical device as a second image;

means for comparing the first and second images produced by the electro-optical device with a specimen image; and means employing the result of said comparison for determining acceptance or rejection of each cigarette fed along the route.

6. Apparatus according to claim 5 in which the electro-optical device receiving the images of the cigarette ends in a single telecamera.

7. Apparatus according to claim 6 in which the first optical device and the second optical device are optical fibre guides.

* * * * *